US010670607B2

(12) United States Patent
Hedman et al.

(10) Patent No.: US 10,670,607 B2
(45) Date of Patent: Jun. 2, 2020

(54) PROTEIN L BASED BIOASSAY METHOD FOR DETERMINING PRESENCE OF SOLUBLE ANTIBODIES IN A SAMPLE AND KIT THEREFOR

(71) Applicant: University of Helsinki, Helsinki (FI)

(72) Inventors: Klaus Hedman, Espoo (FI); Jussi Hepojoki, Helsinki (FI); Satu Hepojoki, Helsinki (FI); Antti Vaheri, Helsinki (FI); Olli Vapalahti, Helsinki (FI)

(73) Assignee: University of Helsinki, Helsinki (FI)

( * ) Notice: Subject to any disclaimer, the term of this patent is extended or adjusted under 35 U.S.C. 154(b) by 546 days.

(21) Appl. No.: 15/121,962

(22) PCT Filed: Feb. 27, 2015

(86) PCT No.: PCT/FI2015/050117
§ 371 (c)(1),
(2) Date: Aug. 26, 2016

(87) PCT Pub. No.: WO2015/128548
PCT Pub. Date: Sep. 3, 2015

(65) Prior Publication Data
US 2017/0067907 A1 Mar. 9, 2017

(30) Foreign Application Priority Data
Feb. 27, 2014 (FI) ...................................... 20145191

(51) Int. Cl.
*G01N 31/00* (2006.01)
*G01N 33/53* (2006.01)
*G01N 33/68* (2006.01)
*G01N 33/542* (2006.01)
*G01N 21/64* (2006.01)

(52) U.S. Cl.
CPC ..... *G01N 33/6854* (2013.01); *G01N 21/6428* (2013.01); *G01N 33/542* (2013.01); *G01N 33/6857* (2013.01); *G01N 2021/6432* (2013.01); *G01N 2333/195* (2013.01)

(58) Field of Classification Search
None
See application file for complete search history.

(56) References Cited

U.S. PATENT DOCUMENTS

| | | | | |
|---|---|---|---|---|
| 5,981,200 A | * | 11/1999 | Tsien | C07K 14/43595 435/183 |
| 7,741,128 B2 | | 6/2010 | Su | |
| 2007/0122852 A1 | | 5/2007 | Bauerle et al. | |
| 2009/0048123 A1 | | 2/2009 | Medintz | |
| 2009/0156421 A1 | * | 6/2009 | Yang | G01N 33/5008 506/9 |

FOREIGN PATENT DOCUMENTS

| | | |
|---|---|---|
| CN | 101278194 A | 10/2008 |
| CN | 101581669 A | 11/2009 |
| CN | 101772514 A | 7/2010 |
| JP | 2010281595 A | 12/2010 |
| WO | 205089409 A3 | 9/2005 |
| WO | 2008020823 A2 | 2/2008 |
| WO | WO-2008020823 A2 * | 2/2008 ........... G01N 33/542 |
| WO | 2008119545 A1 | 10/2008 |

OTHER PUBLICATIONS

Saraheimo et al. (PLoS ONE, 2013, 8(5): e62739, pp. 1-11).*
Tascilar et al. (Annals of Oncology 10,Suppl. 4:S107-S110, 1999).*
Tockman et al. (Cancer Research 52:2711s-2718s, 1992).*
Saraheimo etal. (PLoS ONE, 2013, 8(5): e62739, pp. 1-11) (Year: 2013).*
National Intellectual Property Administration, P.R. China, Search report of Chinese application No. 201580010715.8, dated Sep. 27, 2018, 2 pages.
Saraheimo, Satu et al., Time-Resolved FRET-based Approach for Antibody Detection—A New Serodiagnosis Concept, Plos ONE, May 2013, 11 pages, vol. 8 issue 5.
Chappel, R. J. et al., Immunoassays for the diagnosis of HIV: meeting future needs by enhancing the quality of testing. Future Microbiology 2009, 4(8), 963-982.
Tian, L. et al., Antigen Peptide-Based Immunosensors for Rapid Detection of Antibodies and Antigens, Anal. Chem. 2009, 81, 5218-5225.
Liu, L. et al., Homogeneous Immunoassay Based on Two-Photon Excitation Fluoresence Resonance Energy Transfer, Anal. Chem. 2008, 80, 7735-7741.
Saraheimo, S. et al., Time-resolved FRET-based approach for antibody detection—a new serodiagnostic concept. PLoS One, May 7, 2013, 8(5):e62739 [serial online], [retrieved on Sep. 24, 2014]. Retrieved from the Internet: <URL: http://www.plosone.org/article/info%3Adoi%2F10.1371%2Fjournal.pone.0062739> <doi: 10.1371/journal.pone.0062739>.
Hepojoki, S. et al., A Protein L-Based Immunodiagnostic Approach Utilizing Time-Resolved FÖrster Resonance Energy Transfer, PLoS One, vol. 9, Sep. 2, 2014, p. e106432, XP055190944, DOI: 10.1371/journal.pone.0106432.

(Continued)

*Primary Examiner* — Lisa V Cook
(74) *Attorney, Agent, or Firm* — Berggren LLP (57) ABSTRACT

This invention relates to bioassay method wherein the presence of a specific soluble antibody in a sample of a bodily fluid, plasma or serum, of an animal, including human, is qualitatively and/or quantitatively determined. The method employs, a first group labelled with an energy donor and a second group labelled with an energy acceptor; the first group, or second group, comprising an antigen of the soluble antibody and the second group, or first group, respectively, comprising a Fab binding moiety capable of binding to a Fab region of antibodies of said animal. The donor and the acceptor form an energy transfer pair capable of energy transfer. The invention further comprises a kit for the bioassay method.

15 Claims, 7 Drawing Sheets

(56) References Cited

OTHER PUBLICATIONS

Förster, Von T., Zwischenmolekulare Energiewanderung and Fluorezenz, Annalen der Physik, 1948, vol. 6, pp. 6 55-75.
Ullman, E. F. et al., Luminescent oxygen channeling assay (LOCI): sensitive, broadly applicable homogeneous immunoassay method. Clinical Chemistry, Sep. 1996, vol. 42, No. 9, pp. 1518-1526.
Akerströ, B. et al., Protein L: An Immunoglobulin Light Chain-binding Bacterial Protein. Characterization of Binding and Physiochemical Properties. The Journal of Biological Chemistry, 1989, vol. 264, No. 33, Issue of Nov. 25, pp. 19740-19746.
Chateau, DE M. et al., On the Interaction between Protein L and Immunoglobulins of Various Mammalian Species, Scand J. Immunol., 1993, 37: 339-405.
Björck,, L., Protein L. A novel bacterial cell wall protein with affinity for Ig L chains. The Journal of Immunology, 1988, 140(4): 1194-1197.
Nilson, H. K. et al., Protein L from Peptostreptococcus magnus Binds to the k Light Chain Variable Domain, The Journal of Biological Chemistry, 1992, vol. 267, Issue of Feb. 5, pp. 2234-2239.
Hemmilä, I. et al., Applications of Fluorescence in Immunoassays, Willey & Sons Ltd, New York, 1991.
Hemmilä, I. et al., Time-Resolution in Fluorometry Technologies, Labels, and Applications in Bioanalytical Assays. critical Reviews of Clinical Laboratory Sciences, 2001, 38(6): 441-519.
Mathis, G. et al., Stable Luminescent Chelates and Macrocyclic Compounds, in Hanninen et al. (eds.), Lanthanide Luminesence: Photophysical, Analytical and Biological Aspects, Springer Ser Fluoresc (2011) 7: 47-88, <DOI: 10.1007/4243_2010_5>.
Hemmilä I. et al., Sensitized Bioassays. In Hännien and Härmä (eds.), Lanthanide Luminescence: Photophysical, Analytical and Biological Aspects, Springer Ser Fluoresc (2011) 7: 361-380, <DOI: 10.1007/4243_2010_10>.
Smolander S. et al., A novel antibody avidity methodology for rapid point-of-care serological diagnosis. Journal of Virological Methods, Jun. 2010, vol. 166, No. 1-2, pp. 86-91 <DOI: 10.1016/j.jviromet.2010.02.028>.
Finnish Patent and Registration Office, Search Report dated Oct. 14,0 2014 issued on FI20145191.

* cited by examiner

Intact IgG (Fab)₂

Fab

PROTEIN L BASED BIOASSAY METHOD FOR DETERMINING PRESENCE OF SOLUBLE ANTIBODIES IN A SAMPLE AND KIT THEREFOR

PRIORITY

This application is a U.S national application of the international application number PCT/FI2015/050117 filed on Feb. 27 2015 and claiming priority of Finnish national application number FI20145191 filed on Feb. 27 2014, the contents of both of which are incorporated herein by reference.

FIELD OF THE INVENTION

This invention relates to a method wherein the presence of a specific soluble antibody in a sample of a bodily fluid, preferably plasma or serum, of an animal, including human, is qualitatively and/or quantitatively determined. This invention particularly relates to a separation free serological determination for diagnostic purposes.

BACKGROUND OF THE INVENTION

The publications and other materials used herein to illuminate the background of the invention, and in particular, cases to provide additional details respecting the practice, are incorporated by reference.

A variety of alternatives for serological methods are known in the art. The review on Immunoassays for diagnosing HIV by Chappel et al. [Chappel R J, Wilson K M, Dax E M. Immunoassays for the diagnosis of HIV: meeting future needs by enhancing the quality of testing. Future Microbiology 2009, 4, 963-982] illustrates the known techniques rather comprehensively.

Classical techniques like enzyme-linked immunosorbent assay (ELISA) or enzyme immunoassay (EIA), require extensive washing steps but have a rather high sensitivity and specificity. The downside of such tests is that they require several washing and incubation steps, and thus need quite a lot of hands-on time to perform. Rapid tests, on the other hand, in general, require less time and can be separation free. However, the downside of such tests is that typically rather low sensitivity and specificity can be obtained.

Tian & Heyduk 2009 [Anal Chem. 2009, 81, 5218-5225] have disclosed a homogenous immunosensor design which utilizes bivalent nature of an antibody.

According to Tian & Heudyk 2009 the immunosensor design may find applications in antibody detection, e.g. in diagnosis of autoimmune or infectious disease. The disclosed design employs antigens of antibodies conjugated using flexible linkers with short complementary oligonucleotides each containing a fluorochrome that can form a Foster (or fluorescence) resonance energy transfer (FRET) donor-acceptor pair.

Liu et al. [Anal. Chem. 2008, 80, 7735-7741] proposed homogeneous immunoassays based on two-photon excitation FRET (TPE-FRET). They demonstrated that anti-BSA antibody could be determined using bovine serum albumin (BSA) separately labelled with a donor and acceptor. In vivo or intracellular analysis applications were suggested.

Our previous work [PLOS ONE 2013, 8(5), e62739] described an assay based on measuring TR-FRET between donor-labelled antigen and acceptor-labelled antigen bridged by a specific IgG molecule. The assay disclosed relies on labelling the antigen of interest, in two different reactions, with both acceptor and donor fluorochrome. Since the two labelling reactions are commonly done utilizing different methods for activation, the labelling of antigen with other fluorophores may result in "masking" of the antigens epitopes thus preventing the recognition of the antigen by antibodies.

OBJECT AND SUMMARY OF THE INVENTION

One object of the present invention is to provide a bioassay method for determining the presence of a specific soluble antibody in a sample comprising a bodily fluid.

The present invention provides a bioassay method wherein the presence of a specific soluble antibody of an animal, including human, in a sample comprising a bodily fluid of said animal is qualitatively and/or quantitatively determined, said method employing a) a first group including an energy donor, and
b) a second group including an energy acceptor or quencher,
wherein
i) said first group or said second group comprises an antigen of said soluble antibody, and
ii) said second group or said first group, respectively, comprises a fragment antigen-binding (Fab) binding moiety (FBM) coupled to said energy donor, or said energy acceptor, including quencher, respectively, said moiety being capable of binding to a Fab region of antibodies of said animal, wherein said energy donor and said energy acceptor or quencher form an energy transfer pair capable of energy transfer; and the FBM is selected from the group consisting of protein L, recombinant protein L, Ch1 binding protein, and functional domains, fragments and combinations thereof; preferably recombinant protein L and functional domains, fragments and combinations thereof.

Another object of the present invention is to provide a kit for a bioassay method.

The present invention provides a kit for a bioassay method according to any of the preceding claims, characterized in that said kit comprises i) a first reagent, comprising an energy donor label, and
ii) a second reagent comprising an energy acceptor label or quencher label,
wherein
a) said first reagent or said second reagent comprises an antigen of said soluble antibody of an animal, including human, and
b) said second reagent or said first reagent, respectively, comprises a Fab binding moiety (FBM) coupled to said energy donor, or said energy acceptor or quencher, respectively, said FBM being capable of binding to a Fab region of antibodies of said animal, wherein said donor label and said acceptor label or quencher label form an energy transfer pair capable of energy transfer, preferably Förster resonance energy transfer (FRET), and most preferably time-resolved FRET (TR-FRET), two-photon excitation FRET (TPE-FRET) or luminescent oxygen channelling (LOC); and the FBM is selected from the group consisting of protein L, recombinant protein L, Ch1 binding protein, and functional domains, fragments and combinations thereof; preferably recombinant protein L and functional domains, fragments and combinations thereof.

DETAILED DESCRIPTION OF THE INVENTION

Figure 1:
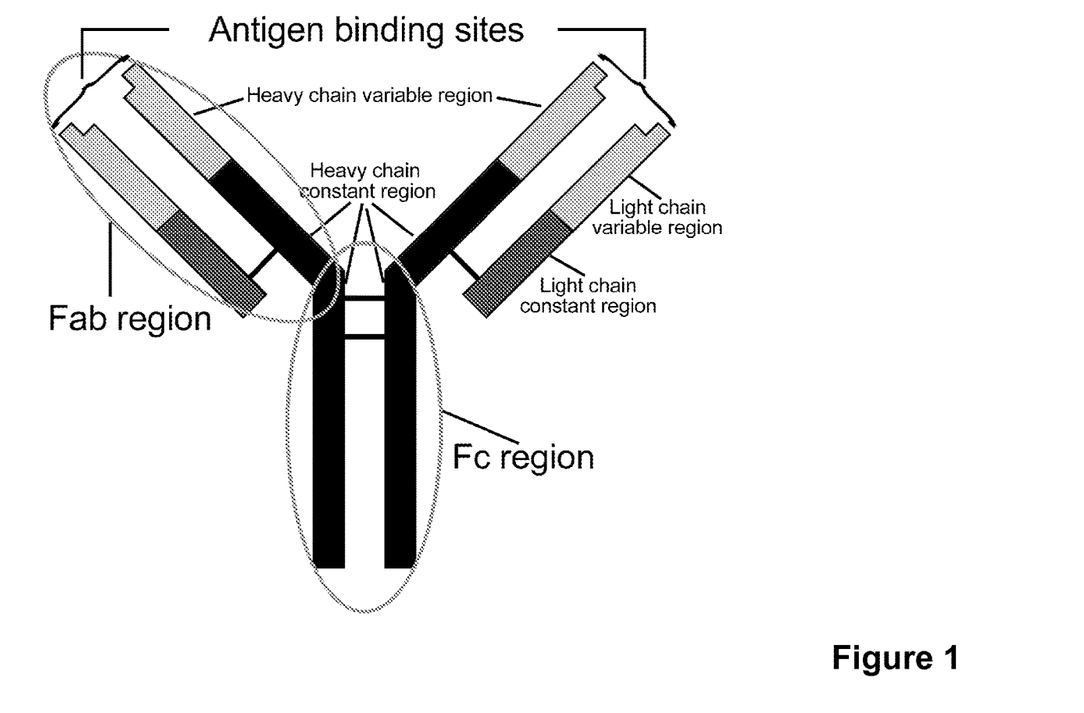
FIG. 1 schematically illustrates the structure of immunoglobulin G molecule.

The present invention utilizes an antigen labelled with a single fluorophore (donor or acceptor) in conjunction with a Fab binding moiety (FBM) labelled with a single fluorophore (donor if acceptor in antigen, and acceptor if donor in antigen). FIG. 1 schematically illustrates the structure of IgG molecule, and the fragments of IgG. The FBM is a moiety capable of binding to light chain, heavy chain, both light and heavy chain, the interface between the light chain and the heavy chain, or the surface formed of the light and the heavy chain in the Fab region, e.g. protein L (a kappa light chain binding moiety). Since the other fluorophore is in the FBM, only a single labelling reaction is required for each antigen, thus minimizing the possibility of the label attaching to amino acids in relevant epitopes that would likely result in inhibition of antigen recognition by respective soluble antibody (due to epitope "masking" by the fluorophore). The use of an FBM that targets light chain (like protein L that is used in our examples) enables the use of the same reagent in the detection of various antigens. Furthermore, if an FBM targeting light chains is used, assays employing such reagents are applicable to the detection of immunoglobulins (Igs) from practically all classes (IgA, IgD, IgE, IgG, and IgM).

Figure 2:
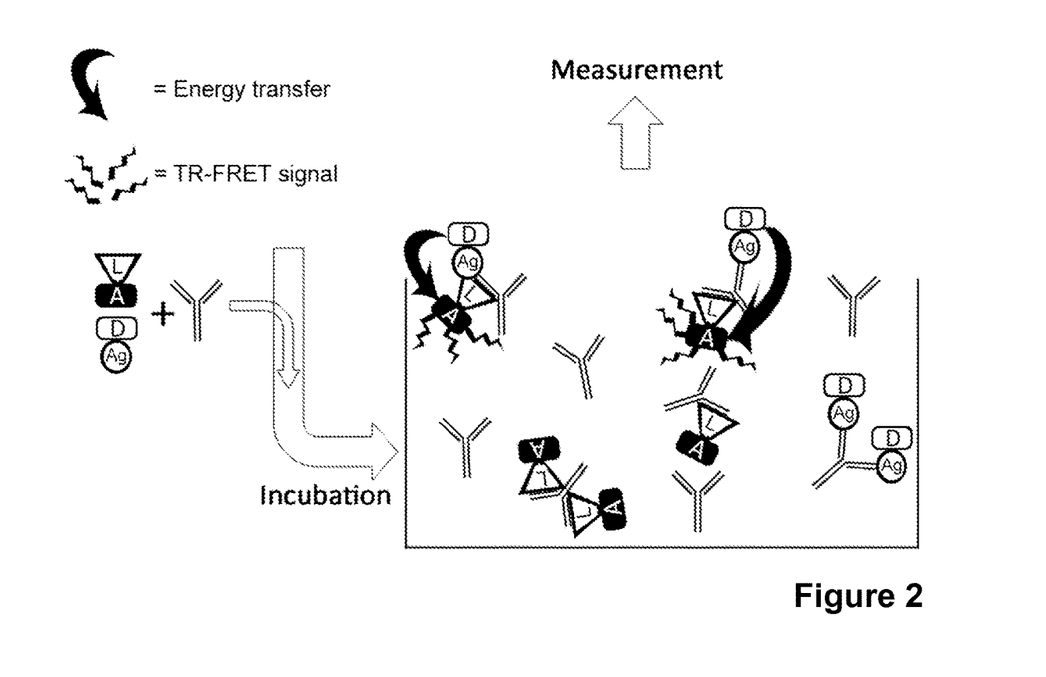
FIG. 2 schematically illustrates the assay principle of the present invention.
Figure 3:
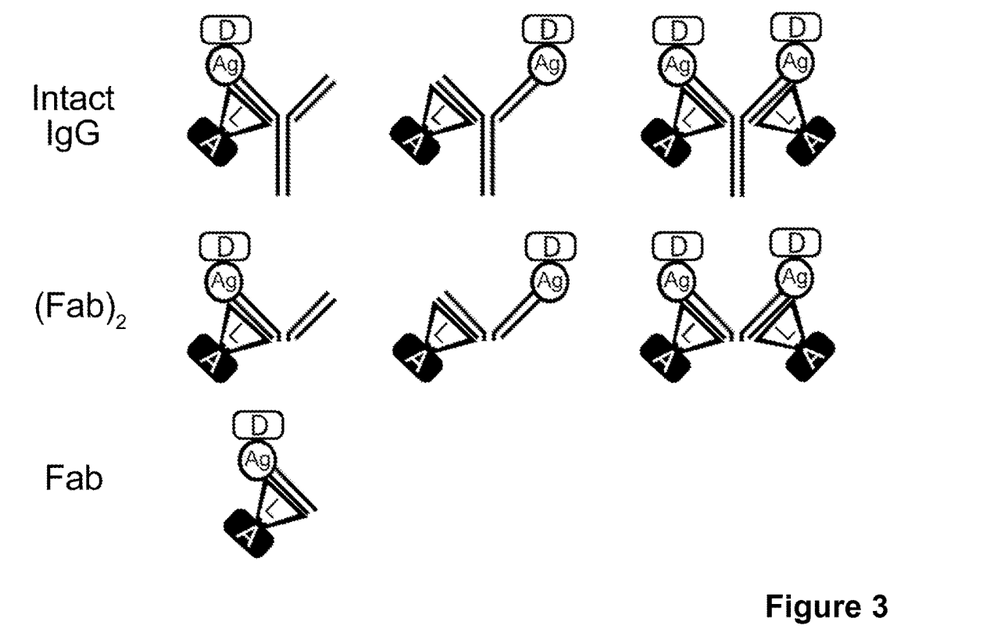
FIG. 3 illustrates the TR-FRET active combinations of antigen and FBM as exemplified in an IgG molecule and its fragments.

FIG. 2 schematically illustrates a typical assay setup of the present invention. When a soluble antibody binds both of the reaction components (fluorophore-labelled FBM as exemplified by protein L, and fluorophore-labelled antigen) in the same Fab-arm or both Fab-arms (or FBM in the other Fab-arm and the antigen in the other), a FRET-pair is formed that can be measured. Only a setup with the donor label (D) in the antigen and the acceptor label (A) in the protein L is shown. The order of labels can be reversed. The antigen-antibody-protein L complexes that are TR-FRET (and FRET) active are schematically exemplified in FIG. 3. The combinations are shown for IgG, but complexes formed by consecutive binding of antigen and protein L to an immunoglobulin molecule of other class (IgD, IgA, IgE, and IgM) are also possible. Also complexes with free light chains with antigen and protein L, would produce TR-FRET signal.

The immunoglobulins comprise heavy chains (humans have $\gamma$, $\delta$, $\alpha$, $\mu$, and $\epsilon$ heavy chains that respectively exist in IgG, IgD, IgA, IgM, and IgE) that complex with light chains (humans have $\kappa$ and $\lambda$ light chains) to form an immunoglobulin molecule. As exemplified in FIG. 1 by the human IgG molecule, the immunoglobulins contain an Fc region that is formed of constant domains in Ig heavy chains and two (or more) Fab regions, each formed of a heavy and light chain (with constant and variable domains in both). Due to the di- or multivalent nature (two or more antigen binding sites i.e. variable regions) of antibodies, it is possible to create homogeneous, i.e. separation free, rapid assays for circulating antibodies by using suitable pairs of reagents, able to generate a signal when brought near each other by binding to the specific soluble antibody. In the present invention a pair of fluorophores capable of energy transfer (exemplified by TR-FRET pair: chelated Europium as donor and ALEXA FLUOR647 as an acceptor) are attached as follows: one fluorophore (donor or acceptor) to a FBM (exemplified by a kappa-light chain binding moiety, protein L) and the other fluorophore (acceptor if donor in FBM and donor if acceptor in FBM) to an antigen, to enable the detection of specific antibodies in a homogeneous assay.

Biochemical assays suitable for such purposes are here called proximity assays. Proximity assays are assays where the specific binding, such as antigen recognition by a soluble antibody, brings sets of two labels into proximity of each other to create an orchestrated signal. Typical such assays are all sorts of energy transfer assays composed of fluorescent or luminescent labels; an energy donor and an energy acceptor, including a quencher. Traditionally such assays are based on two fluorochromes having suitable energetic integral overlapping to allow energy transfer in proximity, within 1-10 nm distances (Förster T, Ann Physik 6:55, 1948).

Other technologies able to monitor reagent proximity in situ are e.g. scintillation proximity assays, bimolecular fluorescence complementation assays, enzyme-fragment complementation assays or oxygen channelling assays. Oxygen channelling assay represents a different energy transfer approach in which the donor label is in donor beads and consists of a photosensitizer composed of phtalocyanine able to generate oxygen radicals upon excitation (Ullman E F et al, *Clin Chem* 1996; 42: 1518-26). The excited oxygen when in proximity (≤200 nm) with acceptor beads, triggers reactions producing emission, e.g. at 613 nm with europium chelate as acceptor. Nanobead-embedded donors and acceptors, suitable for this application are available from PerkinElmer (ALPHA SCREEN® beads, PerkinElmer, Walltham, Mass., USA).

Liu et al. (2008) described a FRET assay to measure bovine serum albumin using two-photon excitation (TPE) FRET (TPE-FRET) between two fluorophores, a donor and an acceptor. FRET has the general limitation that the generated emission is difficult to distinguish from the direct excitation of acceptor, because Förster energy transfer requires a strong spectral overlap, i.e. the excitation of the acceptor has to overlap with the emission of the donor. Due to the narrow Stoke's shift of suitable organic fluorochromes, excitation of the donor inevitable excites the acceptor too. Liu et al. (2008) tried to circumvent the problem using two-photon excitation (TPE), which is an efficient tool to avoid some of matrix (such as that of a serum sample) related background, e.g. scattering. TPE does not, however, avoid the major problem of FRET due to small difference of excitation of donor as compared to acceptor.

Tian & Heyduk (2009) described a combination of FRET and complement hybridization assay to measure circulating antibodies to diagnose immunity. Very close proximity was created in this assay by labelling with short oligonucleotide sequences a set of two antigens labelled either with a FRET donor or acceptor. In the assay complementary sequences are allowed to hybridize, thus bringing the antigens in to close proximity thus creating an exceptionally strong FRET signal. The sequences were optimized so that free antigen-oligo conjugates were not able to efficiently form hybrids. Tian & Heudyk (2009) provided data to show that the principle functions. To be practical, the assay design and labelling is however complicated.

The inventors of the present invention recently developed a TR-FRET-based homogeneous immunoassay, so called FRET-bridge assay, which utilizes donor- and acceptor-labelled antigens (Saraheimo et al., PLOS ONE 2013, 8(5), e62739). In this assay format the simultaneous binding of donor- and acceptor-labelled antigens to an IgG molecule can be measured by TR-FRET, therefore enabling detection of antibodies specific to the given antigen. The FRET-bridge assay was set up utilizing labelled streptavidin (SA), a tetrameric protein, as the antigen. However, when evaluating the performance of FRET-bridge assay using monovalent antigens, they observed that the sensitivity of the assay was decreased. The FRET-bridge assay also requires the antigen to be separately labelled with two fluorophores, which is rather challenging. The labelling chemistries of donor and acceptor are usually different, which may result in the antigens being labelled at different sites. This may result in loss of different epitopes in the two batches of the antigen, which may further lead to prevention of both antigens binding the same antibody. Also, the efficiency of FRET is dependent on the distance between donor and acceptor fluorophores, and thus spatial requirements for FRET also limit the size of the antigen used in FRET-bridge assay.

Figure 4:
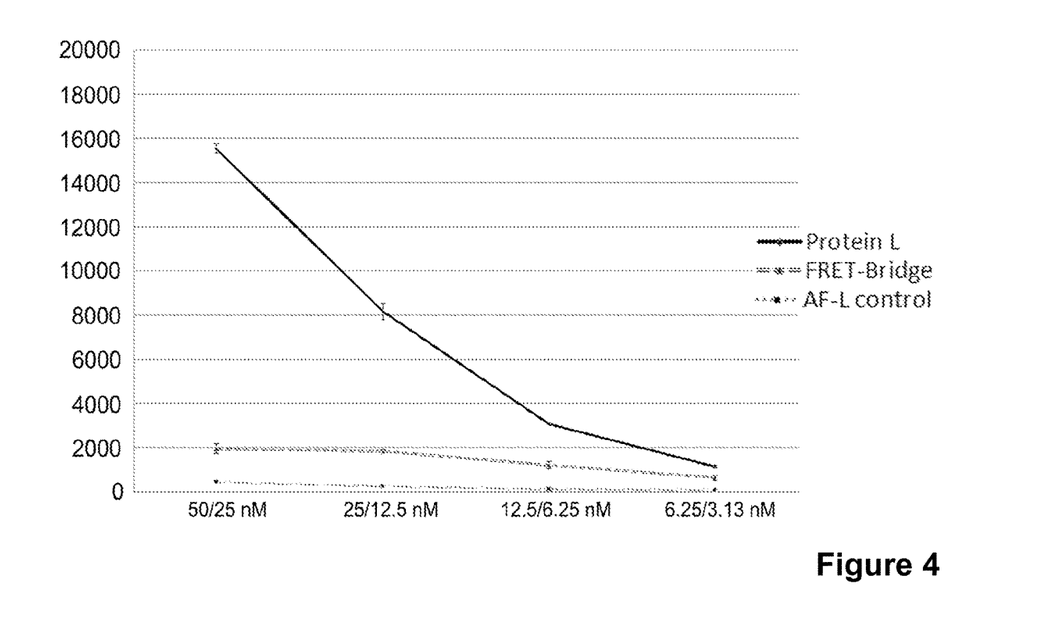
FIG. 4 illustrates comparison between FRET-bridge assay and protein L based assay using SA as the antigen. X-axis shows protein L concentration/antibody concentration at each point.
Figure 5:
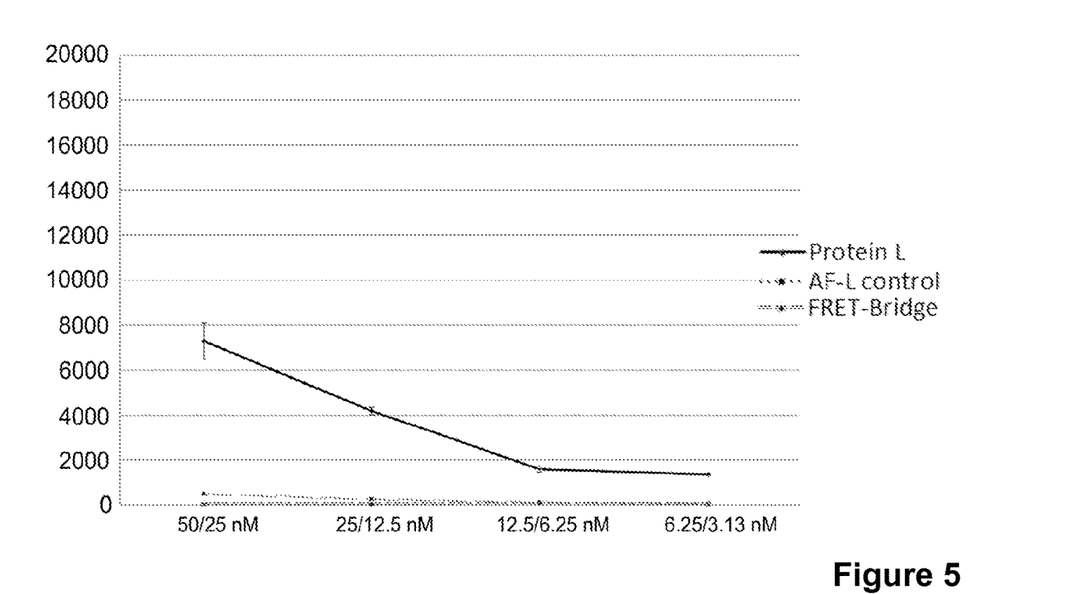
FIG. 5 illustrates comparison between FRET-bridge assay and protein L based assay using GST as the antigen. X-axis shows protein L concentration/antibody concentration at each point.
Figure 6:
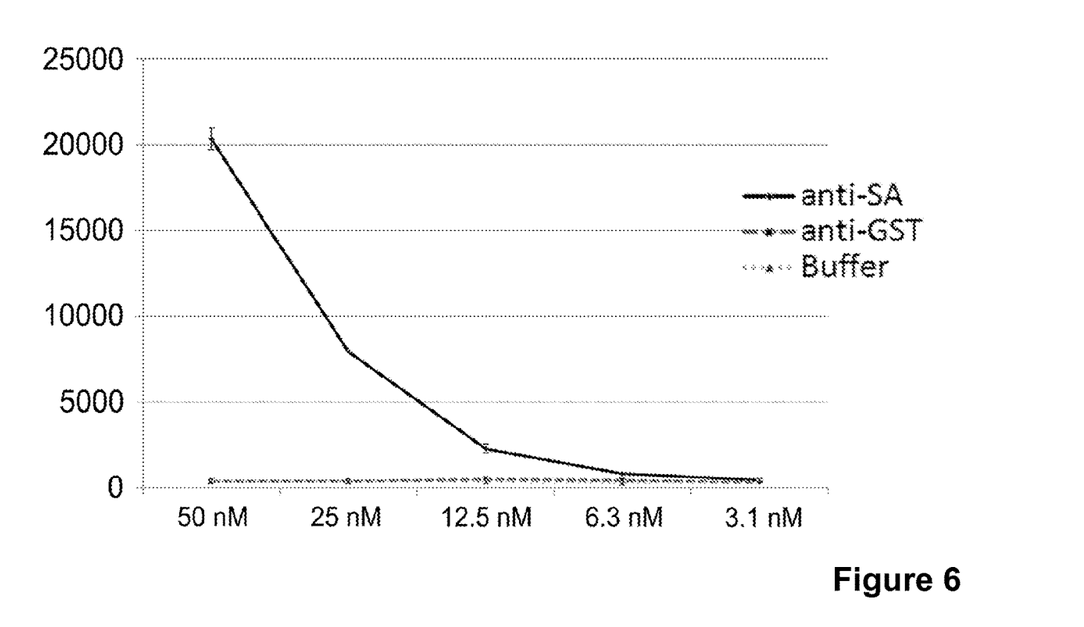
FIG. 6 illustrates anti-SA antibody titrated against Eu-labelled GST-VP1u and AF-labelled protein L with anti-GST soluble antibody as a control (protein L and antigen both 20 nM).

Subsequently the inventors of the present invention decided to test an assay setup using FBM bearing one fluorophore (donor or acceptor) and antigen bearing the other fluorophore (acceptor or donor, respectively). In theory, as exemplified in FIG. 3, the binding of FBM and antigen to a single Fab (or opposite) would bring the FRET-pair forming fluorophores in close enough proximity for the binding to be detected by TR-FRET. The same FBM can be used in the detection of a multiplicity of antigens, and will thus reduce the number of labelling reactions required for setting up assays for different antigens. Moreover, the assay based on labelled FBM (as exemplified by protein L) is highly versatile, since it can be used to detect different soluble antibody subclasses in combination with practically unlimited range of antigens. Surprisingly, the inventors observed that the intensity of TR-FRET signals improved (approximately 7-10 fold increase in signal intensity) with this novel approach as compared to the FRET-bridge assay referred to above (FIGS. 4 and 5). This could reflect either the ability of each soluble antibody molecule to form at least two such complexes, the close proximity of the two fluorophores, and/or the crosslinking function of protein L (incorporating 4 FBMs per molecule).

The inventors of the present invention realized that serological determination of presence of antibodies specific for a given antigen for diagnostic purposes can be carried out simply by employing labelled antigen of the soluble antibody to be determined in combination with an FBM. This can be done by labelling the antigen with a donor (or acceptor) of an energy transfer pair and the FBM with an acceptor (or donor) of the energy transfer pair. Thus, a reaction between a sample, comprising the soluble antibody to be determined, results in that most antibodies will bind acceptor-labelled FBM and some of these antibodies will bind with one or two antigen binding site(s) to the epitope of the antigen labelled with a donor, thus, enabling energy transfer between the donor and acceptor. If the reaction mixture is excited with radiation having an excitation wavelength of the donor, the labelled antigen is excited and energy transfer from the donor to the acceptor ensues, and thereafter the acceptor emits radiation that can be measured. The more antibodies of said specificity the sample contains, the higher the detected signal of emission radiation of the acceptor. If the assay set-up involves a quencher more antibodies in the sample would result in a lower signal, proportional to the antibody concentration.

The example or a proof-of-principle assay utilizes fluorophore-labelled recombinant protein L and fluorophore-labelled antigens (one fluorophore acting as an acceptor, and the other one as a donor) to detect antigen-specific immunoglobulins (exemplified by IgG). Protein L, a bacterial surface protein originally derived from *Peptostreptococcus magnus* (Akerstrom and Bjorck 1989, J Biol Chem 264: 19740-19746), has the ability to bind Ig molecules through kappa light chain without interfering with antigen binding (Akerstrom and Bjorck 1989, J Biol Chem 264:19740-19746). Protein L is capable of binding to all immunoglobulin classes (IgG, IgM, IgA, IgE, and IgD) via their light chains (if kappa chain) (De Chateau et al. 1993, Scand J Immunol 37.339-405). Therefore, protein L binds to a wider range of Ig classes and subclasses than other antibody-binding proteins such as protein A and G (Bjorck 1988, J Immunol 140(4):1194-1197; Nilson et al. 1992, JBC 267: 2234-2239). The binding of these two components, the antigen and the protein L, to the same Fab-arm of a soluble antibody can be measured by TR-FRET, immediately after the binding reaction. This approach does not require washing steps, which means, it is a homogeneous immunoassay. The assay measures the presence or absence of antimicrobial immunoglobulins (IgG and/or IgM) and tells the subject's lifelong exposure record and immunity status (including vaccine-induced) for the studied microbial antigen. In addition to microbial antigens the test as such is suitable for studying reactions towards autoantigens, allergens, etc.

The inventors have comprehended that the reagents, i.e. an antigen labelled with either donor or acceptor and the FBM labelled with an energy transfer pair, surprisingly need no additional functional features and the system can be used to detect the specific antibody response to a given antigen in a bodily fluid with likely 99% of the antibodies in the bodily fluid targeting other, unrelated antigens. As long as the labels do not interfere with the ability of the soluble antibody, to be detected, to bind to the epitope of the labelled antigen or the FBM, the bioassay of the present invention is, in principle, functional. Intrinsically the Fab arms of immunoglobulins, with the antigen binding sites, will enable the binding of both antigen and the FBM.

The idea of the present invention can in principle be carried out employing any energy transfer pair and/or proximity based assay. However, considering the aim of providing a simple assay and that serological samples typically involve a complex sample matrix, alternatives effectively eliminating background emission, e.g. by sample matrix components, are to be preferred.

Definitions

The term soluble antibody and antibody refers, as would be apparent to a person skilled in the art, in the context of this application to soluble antibodies. Since the present invention is particularly directed to serological determination for diagnostic purposes, membrane-bound antibodies, e.g. B cell receptors (BCR), are not of interest and accordingly not referred to.

The term bodily fluid in the context of this application refers to any fluid within or excreted from the body of an animal, including human. Bodily fluid thus refers to e.g. blood, its constituents plasma and serum, cerebrospinal fluid, saliva, urine, nasopharyngeal and bronchoalveolar secretion, aspirate or lavage fluid, ocular fluids, pleural fluid, exudate and ascites, semen, bile and effusions (e.g. from middle ear or paranasal sinuses). Bodily fluid particularly refers to plasma, serum and cerebrospinal fluid.

The term antigen in the context of this patent refers to an antigen, a haptenic antigen or a fragment of antigen containing pertinent epitopic site.

The term Fab binding moiety (FBM) in the context of this application refers to a molecule, preferably a polypeptide i.e. protein, that is capable of binding to light chain, heavy chain, both light and heavy chain, the interface between the light chain and the heavy chain, or the surface formed of the light and the heavy chain in the Fab region of Ig molecule. FBM may bind either constant or variable domain in the Fab region of an immunoglobulin. The FBM is particularly selected from the group consisting of protein L, recombinant protein L, Ch1 binding protein, and functional domains, fragments and combinations thereof; preferably recombinant protein L and functional domains, fragments and combinations thereof. "Functional domains, fragments and combinations thereof" refers to domains and/or fragments of protein L, recombinant protein L and Ch1 binding protein that comprise at least one domain or fragment with the capability of binding to light chain, heavy chain, both light and heavy chain, the interface between the light chain and the heavy chain, or the surface formed of the light and the heavy chain in the Fab region of Ig molecule.

The term label and labelling in the context of this application refers to a detectable label molecule, which may comprise a fluorescent compound, suitable metallic element, e.g. lanthanide, or chelates thereof, fluorescent or energy accepting, it may also be a nanobead embedded with fluorescent or quenching compounds, or a photosensitizer, fluorescent nanodots, chelate-embedded beads, quantum dots as acceptors, upconverting crystal or nanobeads containing those. In the context of this application the labels, described above, can be directly, covalently or non-covalently, coupled to defined antigens, or they may be attached by indirect means, such as through the interaction of avidin or streptavidin with a biotinylated component, using antibodies, such as anti-digoxigenin or anti-fluorescein, or anti-species anti-IgG antibodies, lectins, oligonucleotides or other generally used indirect ways of labelling.

The term energy transfer is to be understood broadly as a signal generation where the donor, upon excitation by electromagnetic radiation, typically light, is able, by non-radiative, radiative, or intermediate means, to transport energy to the acceptor, which may eventually quench the donor signal or accept the energy and generate a different signal. A donor is a compound able to absorb energy, e.g. by excitation radiation, and in close proximity to a suitable acceptor or quencher, will donate the energy to the acceptor or quencher (by a suitable mechanism such as Förster resonance energy transfer, FRET). The acceptor can be coloured, fluorescent or non-fluorescent organic compound. It can also be an organometallic compound, or a metallic nanobead, a quantum dot, a nanodot, or a nanobead containing suitable energy accepting compounds. Typical, but not limiting technologies, are various types of FRETs, quenching reactions and oxygen channelling reactions. Time-resolved FRET (TR-FRET) is a technology employing the excited state difference of donor and acceptor, hence using time-resolution (gated detection) in detection. Specific examples of energy transfer are TR-FRET using lanthanides and chelates thereof, or lanthanide embedded beads as donors, using lanthanide containing upconverted crystals as acceptors, or lanthanide-containing beads as final acceptors in LOC.

PREFERRED EMBODIMENTS OF THE INVENTION

Labelling of antigens for the assay according to the invention depends on the system of choice. For FRET and TR-FRET type of assays the most efficient way technically is to covalently label the antigens or their fragments and the FBM with respective sets of donors and acceptors. The total amount of labels per antigen or fragments and the FBM depends e.g. on their size. Higher number of labels enables good proximity of at least one label pair in the formed complex, unless labelling blocks the epitopic sites and prevents the reaction.

For practical assay optimization an alternative is to use an indirect labelling procedure, employing biotinylated antigens and sets of two avidin/streptavidins labelled with donors and acceptors, respectively, or combining biotin with another binding pair (e.g. hapten anti-hapten).

The preferred way to use FRET in this invention is to use time-resolution to distinguish donor and acceptor emission from the created energy-transfer activated emission. By using temporal resolution one can improve signal specificity and also avoid all ambient sample and reagent related background problems (Hemmila I, Applications of fluorescence in immunoassays, Willey & Sons Ltd, New York, 1991). Preferred pairs of labels consists of fluorescent Eu chelates (see e.g. Hemmila I and Mukkala V-M; Crit Rev Clin Lab Sci 2001; 38; 441-519, Mathis G and Bazin H, Lanthanide Luminescence, Springer, Heidelberg, pp 47-88) together with suitable acceptors, such as allophycocyanin, Cy-5, some rhodamines, ALEXA FLUOR 647 or similar product from other sources (HiLight, DyLight, Ulight etc) (Hemmila I and Laitinen V, Lanthanide Luminescence. Springer. Heidelberg, pp. 361-280) Similarly a preferred label pair consists of fluorescent terbium (Tb) chelates and sets of acceptors, such as rhodamine, fluorescein, Cy-3. Also nanobeads composed of the above mentioned chelates can be used as donors. Acceptors may include quantum dots, nanodots, nanobeads, nanobeads embedded with fluorescent or quenching compounds, a photosensitizer, chelate-embedded beads, upconverting crystals, or nanobeads comprising any of the aforementioned.

Similarly in LOC assay principle, a preferred set of labels comprises donor beads containing phthalocyanine, and acceptor beads containing suitable chemiluminescence reaction and Eu diketone chelates as acceptors, those beads being readily available from Perkin Elmer.

In many preferred bioassay methods according to the invention the soluble antibody is a human soluble antibody. In some preferred bioassay methods according to the invention the soluble antibody is an animal, excluding human, soluble antibody.

A typical bioassay method according to the invention comprises the steps of
a) contacting the sample, the first group, and the second group to obtain a reaction mixture,
b) allowing the reaction mixture react,
c) exciting the energy donor with radiation having an excitation wavelength thereby forming an excited labelled antigen
d) detecting emission radiation from
  i) the acceptor resulting from energy transfer from the donor, whereby an increased emission signal correlates with an increased level of the specific first soluble antibody in the sample, or
  ii) the donor if a quencher is employed, whereby a decreased emission signal of the donor correlates with an increased level of specific first soluble antibody in the sample.

In many preferred bioassay methods of the invention the sample and the group comprising the FBM are contacted in step a), and allowed to react; and then the group, first or second, comprising the antigen is added.

In some preferred bioassay methods of the invention step a) comprises two consecutive phases,
  i) a first phase wherein the sample is contacted with an immobilized capturing immunoglobulin whereby the soluble antibody of the sample is captured by said capturing immunoglobulin, and thereafter
  ii) a second phase wherein said captured soluble antibody of said sample is contacted with the first group and the second group to obtain the reaction mixture.

In some preferred bioassay methods of the invention step a) comprises addition of a kosmotropic, chaotropic, precipitating, and/or outsalting reagent such as, but not limited to, ammonium sulphate, polyethylene glycol (PEG), organic solvent, salt, urea, guanidine, acid or base.

In some preferred bioassay methods of the invention the detection of emission is carried out at least twice,
  i) once when a denaturing or chaotropic agent is included in the reaction mixture, and
  ii) once when said denaturing and/or chaotropic agent is not included in the reaction mixture,
whereby the difference in emissions correlates with the avidity of the soluble antibody if present. In such bioassay methods the denaturing and/or chaotropic agent is preferably selected from the group consisting of sodium dodecyl sulphate (SDS), urea, thiocyanate, guanidine and diethylamine.

In preferred bioassay methods of the invention the bodily fluid is selected from the group consisting of blood, plasma, serum, cerebrospinal fluid, saliva, urine, nasopharyngeal secretion, bronchoalveolar secretion, aspirate fluid, lavage fluid, ocular fluid, pleural fluid, exudate, ascites, semen, bile, effusions and any combination thereof; preferably plasma, serum and cerebrospinal fluid.

In preferred bioassay methods of the invention the soluble antibody is selected from the group consisting of human immunoglobulins A, D, E, G (including subclasses 1, 2, 3 and 4), and M; and corresponding immunoglobulins of other species (e.g. IgY is considered the avian and reptilian equivalent of IgG), preferably corresponding to the group consisting of human immunoglobulins A, E, G (including subclasses 1, 2, 3 and 4), and M.

In preferred bioassay methods of the invention the soluble antibody is selected from the group consisting of antibodies against antigens selected from the groups consisting of microbial antigens, including bacteriological, parasitic, fungal and viral antigens; exogenous antigens; autoantigens; allergens; and tumour antigens.

In preferred bioassay methods of the invention the energy transfer pair is capable of Förster resonance energy transfer (FRET). In such bioassay methods the bioassay is preferably a time-resolved FRET (TR-FRET) assay or a two-photon excitation FRET assay.

In some preferred bioassay methods of the invention the assay is a luminescent oxygen channelling (LOC) assay.

In many preferred kits of the present invention the soluble antibody is a human soluble antibody. In some preferred kits of the present invention the soluble antibody is an animal, excluding human, soluble antibody.

In many preferred embodiments of the kit of the present invention the ratio of the amount of donor of the first reagent, or second reagent, to that of the amount of acceptor, including quencher, of the second reagent or first reagent, respectively, is
  i) at least 10%, preferably at least 90%, and
  ii) not more than 1000%, preferably not more than 120%, and
  iii) most preferably about 100%,
wherein a ratio corresponding to 100% is obtained by an equivalent amount of donor to acceptor, including quencher.

EXAMPLES

Example 1

Proof-of-Principle, a Protein L Based Homogeneous (Solution Phase) TR-FRET Assay for the Detection of Soluble Antibodies Methods Recombinant protein L was purchased from Thermo Scientific (Pierce Protein Biology Products) and separately labelled with QuickAllAssay Eu-chelate protein labelling kit (BN products & Services Oy) and ALEXA FLUOR® 647 (AF647) Protein Labelling Kit (Invitrogen). Labelling was performed according to the manufacturers' instructions AF647 and Eu-chelate-labelled streptavidin (AF647-SA and Eu-SA, respectively) were ordered from Invitrogen and PerkinElmer, respectively. The unique region of human parvovirus B19 (B19V) minor capsid protein VP1 was expressed in *E. coli* as GST-fusion protein (here denoted as GST-VP1u), purified and independently labelled with Eu (using the QuickAllAssay Eu-chelate protein labelling kit of BN Products & Services Oy) and AF647 (using the Protein Labelling Kit of Invitrogen) according to the manufacturers' instructions. GST-VP1u served as antigen for experiments with anti-GST antibodies. Monoclonal antibody (MAb) against SA (anti-SA) (clone S3E11, 6.1 mg/ml) was purchased from Thermo Scientific (Pierce Protein Biology Products). Monoclonal anti-GST was from Abcam Ltd (1 mg/ml) and IgG-free bovine serum albumin (BSA) from Jackson ImmunoResearch Inc.

TR-FRET values were measured with Wallac Victor$^2$ fluorometer (PerkinElmer) by excitation at 320 nm followed by a delay of 70 μs before recording fluorescent counts for 100 μs with 615 nm (Eu) and 665 nm (AF647) emission filters. To take into account the emission of Eu at 665 nm the measured TR-FRET values were normalized according to the following equation: AF647N=AF647-k*Eu, where AF647N=normalized AF647 fluorescent counts, AF647=unnormalized A647 counts (at 655 nm), k=Eu emission at 665 nm/Eu emission at 615 nm and Eu=Eu fluorescent counts (at 615 nm). The constant k was found to be independent of Eu-SA concentration whereby a value of 0.001342 (average of AF647- to Eu-counts in Eu-SA dilutions of 1:1000 to 1:8000) was used in subsequent calculations.

The basic protocol for all TR-FRET assays was as follows: after the reaction components were diluted in Tris-buffered saline (TBS; 50 mM Tris-HCl, 150 mM NaCl [pH 7.4]) supplemented with 0.2% BSA (TBS-BSA), protein L was mixed 1:1 with MAb, incubated for 15 min at +37° C. and mixed 1:1 with the labelled antigen. The final reaction volume (20 μl/well) was pipetted onto a 384-well microplate (ProxiPlate-384 Plus F, Black 384-shallow well Microplate from PerkinElmer).

Results

Figure 7:
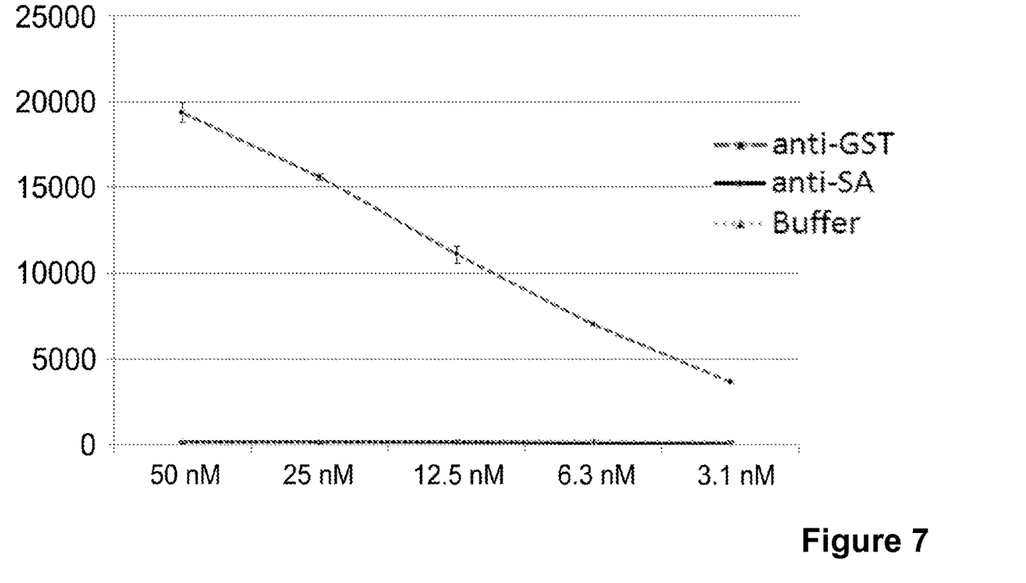
FIG. 7 illustrates anti-GST antibody titrated against Eu-labelled SA and AF-labeled protein L with anti-SA antibody as a control (protein L and antigen both 20 nM).
Figure 8:
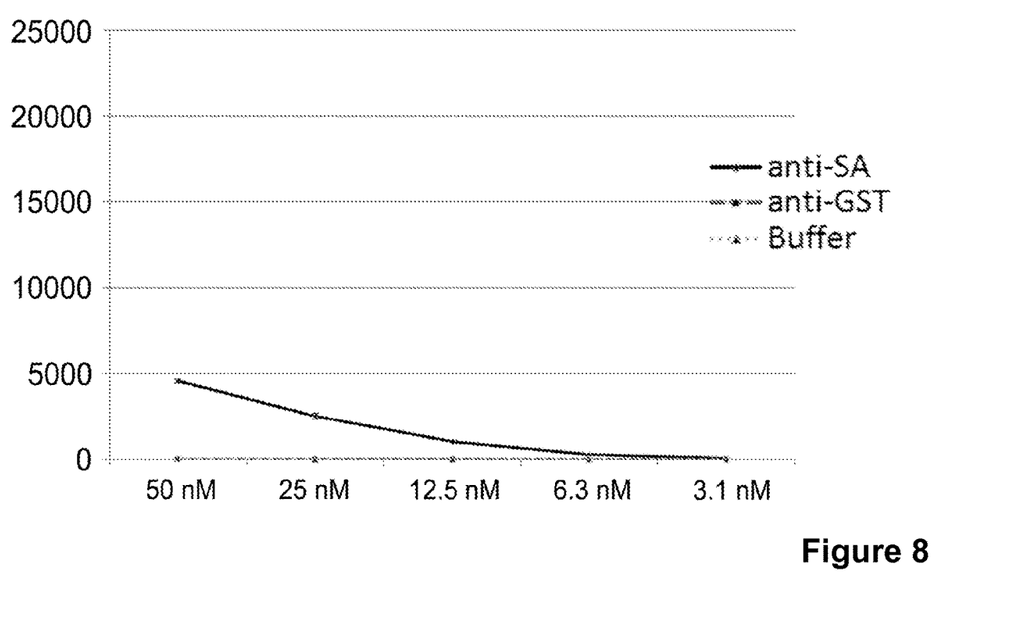
FIG. 8 illustrates anti-SA antibody titrated against AF-labelled SA and Eu-labelled protein L with anti-GST antibody as a control (protein L and antigen both 20 nM).
Figure 9:
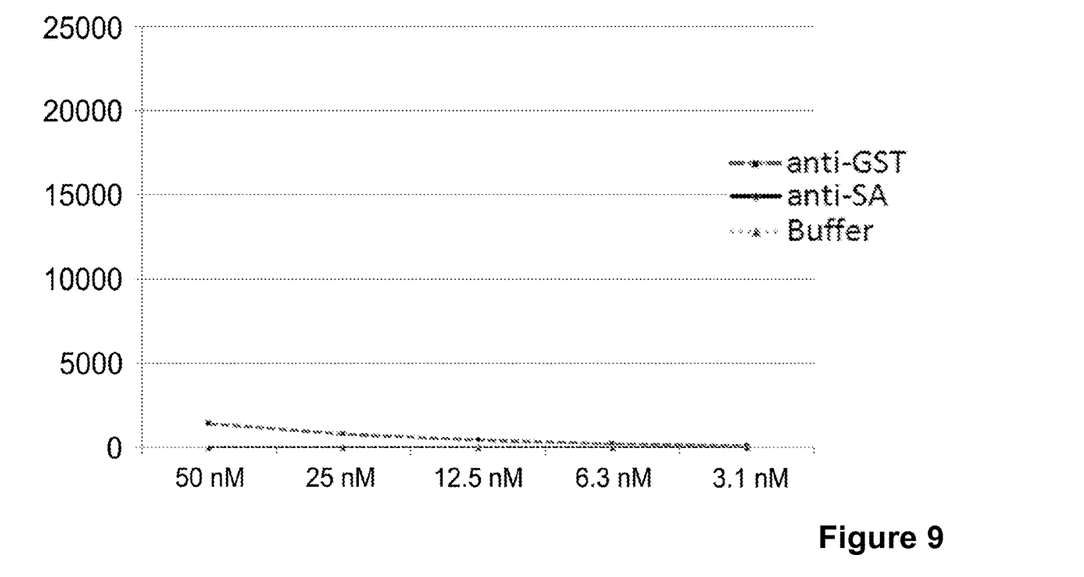
FIG. 9 illustrates anti-GST soluble antibody titrated against AF-labelled GST-VP1u and Eu-labelled protein L with anti-SA soluble antibody as a control (protein L and antigen both 20 nM).

To assess the optimal amounts of protein L and antigens relative to antibody concentrations, we titrated the antibodies (anti-GST and anti-SA at 50 nM-3.1 nM) against constant concentrations of the antigens (Eu- or AF-labeled SA and GST-VP1u at 20 nM) and protein L (Eu- or AF-labeled at 20 nM). In the experiments with anti-SA MAb, anti-GST MAb served as control, and vice versa. With AF-labeled protein L and Eu-labeled antigens both streptavidin (FIG. 4) and GST (FIG. 7) induced TR-FRET signals dose-dependently with antibody concentrations. However, when the donor label (Eu) was in protein L, AF-SA (FIG. 8) induced markedly higher TR-FRET responses than did AF-GST-VP1u (FIG. 7). TR-FRET signals close to measured background were detected in the presence (or absence) of the control antibodies in both experimental setups (AF-L and Eu-L, FIGS. 6-9).

Example 2

Protein L Based TR-FRET Assay Relies on Simultaneous Binding of Antigen and Protein L to a Single Fab Fragment Methods The anti-SA MAb (S3E11) was fragmented using papain as earlier (Saraheimo et al. PLOS ONE 2013, 8(5), e62739), briefly, papain 25 mg/ml, 40 U/mg, (P3125, Sigma-Aldrich) was diluted 1 to 10 in 100 mM L-cysteine (in PBS, pH 7.4) and preactivated by 15 min incubation at RT. Anti-SA MAb was diluted 1 to 3 in reaction buffer (10 mM L-cysteine and 10 mM EDTA in PBS) yielding a 2 mg/ml antibody solution. Preactivated papain was further diluted 1 to 100 in reaction buffer. The cleavage reaction was set up by mixing 1 part of papain solution with 1 part of diluted antibody. The cleavage was carried out at 37° C. for 4 h, after which papain was inactivated by addition of 0.3 M iodoacetamide (in PBS) to reach final concentration of 30 mM. Adsorption with GAMMABIND™ PLUS SEPHAROSE™ (GE Healthcare) was used to remove intact IgG molecules and to roughly separate the cleavage products (Fab and Fc parts) from each other. Briefly, GAMMABIND™ beads were equilibrated to PBS+ (PBS with additional 150 mM NaCl and 0.01% of TWEEN 20), mixed with the reaction mixture and incubated 15 min at RT. The beads were sedimented by centrifugation (500×g, 2 min) and the supernatant recovered. The beads were washed twice with 150 μl of PBS+ and the resulting supernatants were pooled together with the initial supernatant. The supernatant pool containing the Fab fragments and inactivated papain was concentrated and the buffer exchanged to PBS using Amicon Ultra 10 kDa centrifugal filter units (Millipore) according to product instructions.

Results

Figure 10:
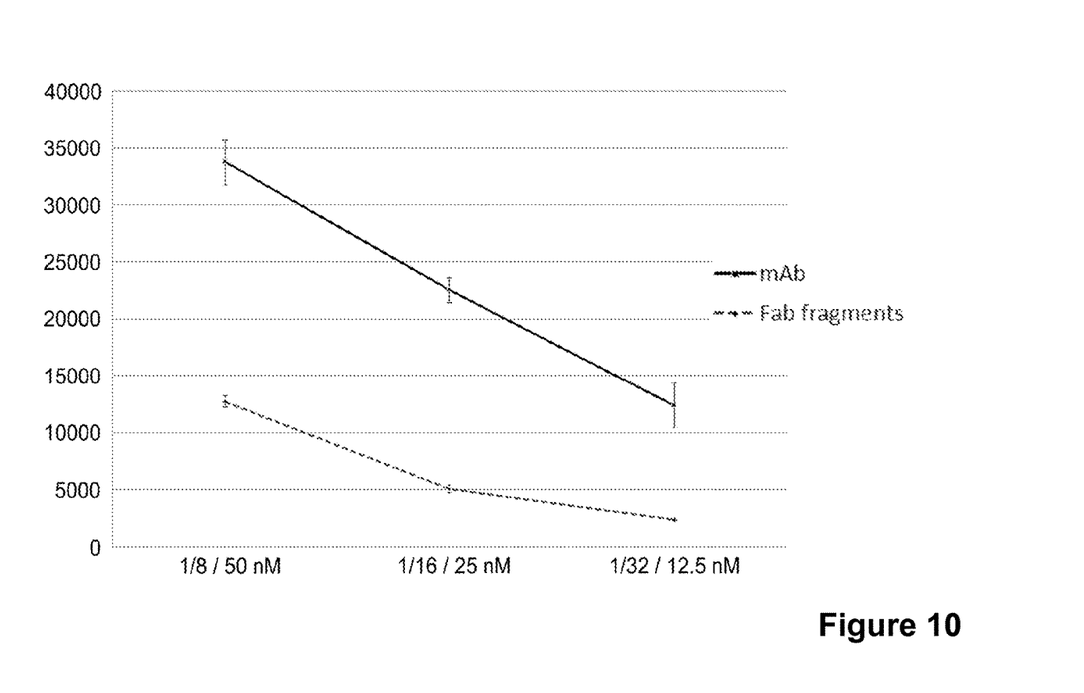
FIG. 10 illustrates anti-SA Fab-fragments (1/8 to 1/32 dilution) and intact anti-SA (50 to 10 nM) titrated against constant protein L (acceptor labelled) and antigen (donor labelled) concentration (20 nM each).

We serially diluted the anti-SA Fab-fragments and antibodies and mixed them separately with labelled protein L and SA. As shown in FIG. 10, Fab fragments produce a dose-dependent increase in TR-FRET signals, analogously to the signals induced by the MAb. The signal intensities induced by Fab fragments were approximately half of those induced by the MAb, which reflects the lower concentration of the Fab fragments as compared to the concentration of the MAbs. The results confirm that TR-FRET can originate from a single Fab fragment.

Example 3

Comparison to FRET-Bridge Assay

Methods

The assay for protein L based application was as described above. The concentrations of the corresponding MAbs (anti-SA and anti-GST) and of the AF-labeled protein L were varied, while that of the antigens (Eu-SA and Eu-GST-VP1u) was kept constant (10 nM). The antibody concentrations ranged from 25 nM to 3.1 nM, while the protein L concentration was always two-fold higher than that of the antibody (50 nM to 6.3 nM). For the FRET-bridge assay, the final reaction mixture (20 μl) consisted of 10 μl of the antigen mix and 10 μl of antibody solution that were dispensed onto a 384-well microplate. The antigens and antibodies were diluted in TBS supplemented with 0.2% bovine serum albumin (BSA).

Results

Both of the antigens, SA and GST-VP1u, induced higher TR-FRET signals in the protein L assay (FIG. 4 vs. FIG. 5, respectively). In fact, the GST-VP1u antigen did not induce any signal in the FRET-bridge assay (FIG. 5), augmenting our previous hypothesis (Saraheimo et al. PLOS ONE 2013, 8(5), e62739) that in the FRET-bridge assay the multimericity of the antigen is beneficial. We have previously also observed that most of the TR-FRET activity is derived from large immunocomplexes, the formation of which actually might be inhibited by monomeric antigens. In the protein L assay, SA induced twice higher TR-FRET signals compared to GST-VP1u. Hence, it seems possible that also in the protein L approach, multimericity of the antigen is beneficial, even if not obligatory.

Example 4

Figure 11:
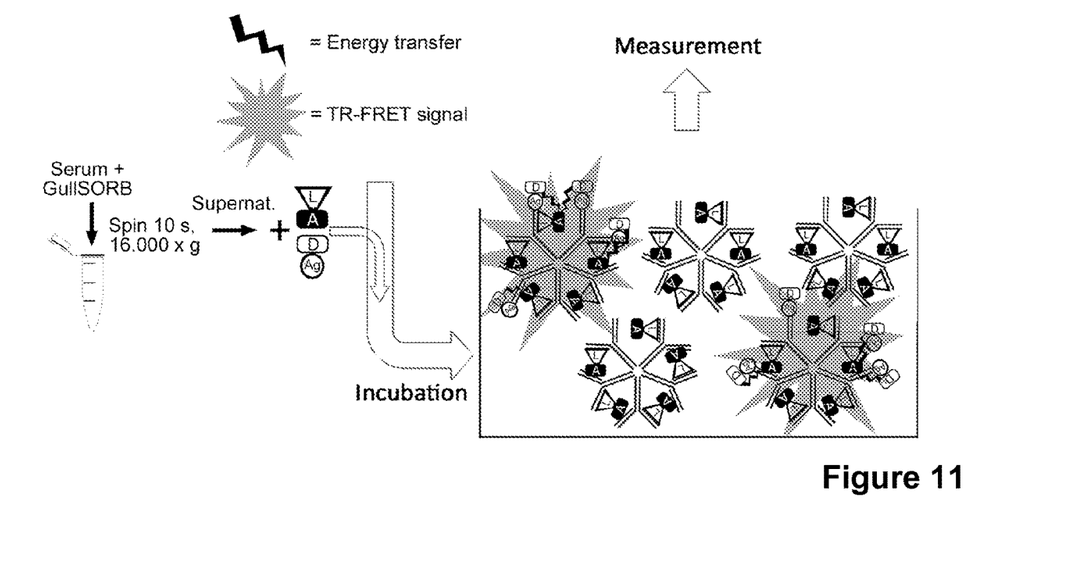
FIG. 11 schematically illustrates the assay principle of the present invention when employing GuIISORB to remove IgGs by centrifugation.

Protein L Based Homogeneous (Solution Phase) TR-FRET is Applicable for the Detection of Serological Response, Proof-of-Principle Methods Puumala virus (PUUV), a zoonotic pathogen, may induce a mild hemorrhagic fever with renal syndrome (HFRS) when transmitted to man. The infection induces a strong serological response (both IgM and IgG are practically always present at the time of diagnosis) against the nucleocapsid (N) protein of PUUV. Recombinant PUUV N protein was purchased from Reagena ltd (Finland) and Eu-labelled using QuickAllAssay Eu-chelate protein labelling kit (BN products & Services Oy) according to the manufacturers' instructions. AF647 labelled recombinant protein L was prepared as described in example 1. Two assay formats, schematically depicted in FIG. 2 and FIG. 11, were set up for the evaluation of assay performance. The assay depicted in FIG. 2 is designed to detect both IgM and IgG against a given antigen and, actually all antigen specific Ig classes. The assay depicted in FIG. 11 is designed to detect Ig classes other than IgG, mainly IgM. Prior to performing the assay depicted in FIG. 11 the analyte (the solution to be studied, serum in this example) is mixed with GulISORB reagent (Meridian Bioscience Inc.) and the IgGs are removed by centrifugation. The assay components, AF647 labelled protein L and Eu-labelled PUUV N protein, were diluted in TBS-BSA and dispensed onto a 384-well microplate (Proxi-Plate-384 Plus F; black 384-shallow-well microplate from PerkinElmer), and 5 µl of serum dilution was added. After 30 min at 37° C., the TR-FRET values were measured with Wallac Victor$^2$ fluorometer (PerkinElmer) and the values were normalized as described in example 1. All experiments were performed in duplicate. After optimizations 25 nM protein L and 5 nM PUUV-N were used with 1/100 serum dilution. The TR-FRET signals of samples were compared to the TR-FRET signal induced by a pool of negative control sera (the average of normalized TR-FRET value divided by the average of normalized TR-FRET value from the negative control, a pool of PUUV-negative control sera), and the test values were reported as integers.

Results

Figure 12:
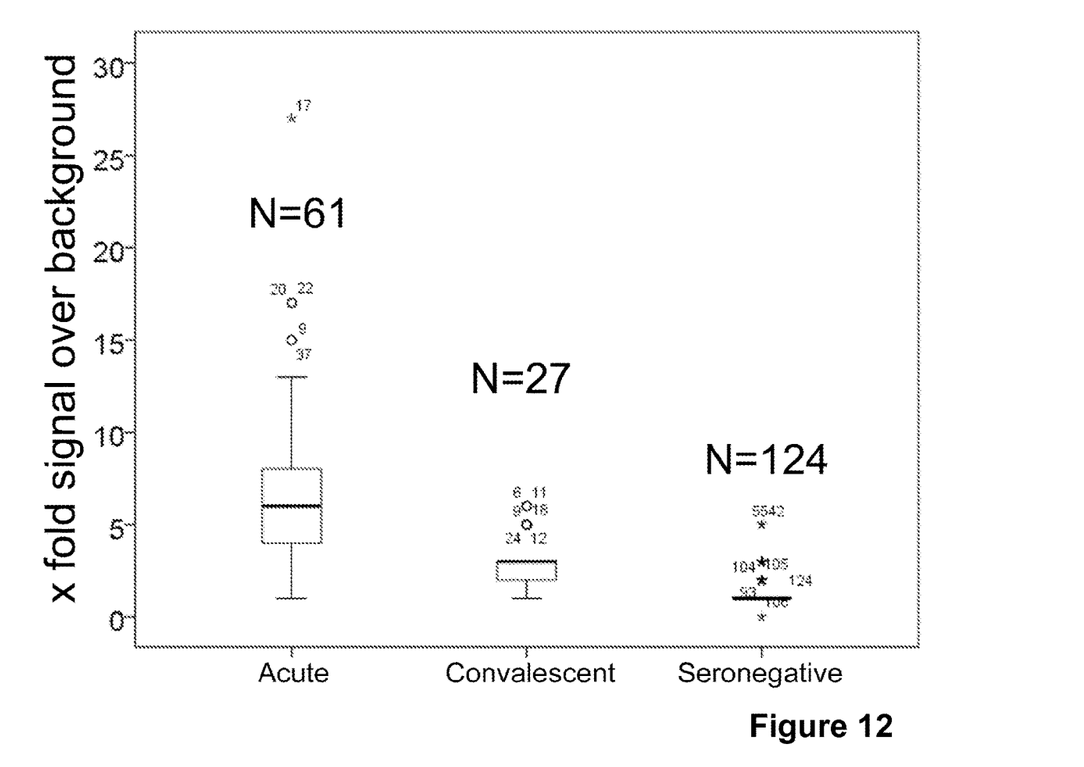
FIG. 12 illustrates test results of 211 serum samples.
Figure 13:
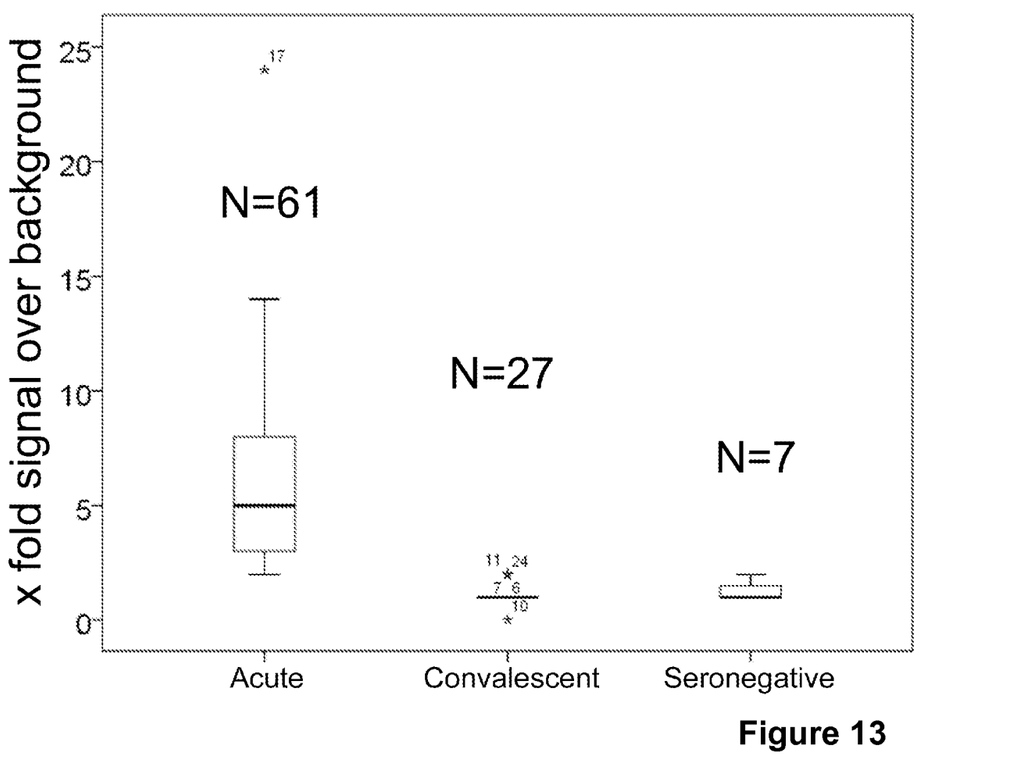
FIG. 13 illustrates test results of 211 serum samples when employing GuIISORB to remove IgGs by centrifugation.

We evaluated the test by studying 211 serum samples (table 1): 61 acute, 27 convalescent/past infection, and 123 seronegatives. Using a well-characterized serum panel, we set the protein L TR-FRET assay threshold at a signal level 3-fold over background (values ≥3 times the TR-FRET signal obtained with a negative serum pool are considered positive). With the test setup described in FIG. 2, 59 of the 61 acute-phase and 14 of the 27 past-infection samples were identified as PUUV seropositive (table 1 and FIG. 12). Seven of the 123 PUUV seronegative samples yielded a false positive result in the protein L TR-FRET assay (table 1 and FIG. 12). When the serum samples were pre-treated with GulISORB, 58 of the 61 acute-phase and none of the past and seronegative samples yielded a positive result in the protein L TR-FRET assay (table 1 and FIG. 13). These results provide the proof-of-principle for the applicability of protein L TR-FRET assay in-solution for the detection of antibodies using human serum as the sample material.

TABLE 1

Test results of 211 serum samples

| Test result | | Acute (IgG+ and IgM+, N = 61) | | Past (IgG+ and IgM−, N = 27) | | Negative (IgG− and IgM−, N = 123) | |
|---|---|---|---|---|---|---|---|
| | | Protein L assay | Reference | Protein L assay | Reference | Protein L assay | Reference |
| Without IgG removal (FIG. 2 setup) | + | 59 | 61 | 14 | 27 | 7 | 0 |
| | − | 2 | 0 | 13 | 0 | 116 | 123 |
| After IgG removal (FIG. 11 setup) | + | 58 | ND | 0 | ND | 0 | ND |
| | − | 3 | ND | 27 | ND | 123 | ND |

Example 5

Luminescent Oxygen Channelling Assay

Luminescent oxygen channeling (LOC) assay format can be applied to the present invention by e.g. obtaining donor and acceptor beads surface-coated with streptavidin available from PerkinElmer, and antigen labelled with biotin. The Envision plate-reader available from PerkinElmer can be used to measure the signal produced upon bead excitation at 613 nm.

Other Preferred Embodiments

It will be appreciated that the methods and kits of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A bioassay method, wherein the presence of a soluble antibody of an animal, including a human, in a sample comprising a bodily fluid of said animal, is qualitatively and/or quantitatively determined, said method comprising:
   a) providing a first group including an energy donor;
   b) providing a second group including an energy acceptor including a quencher, wherein
      i) said first group or said second group comprises an antigen of said soluble antibody, said antigen coupled to said energy donor, or said energy acceptor including the quencher, and
      ii) said second group or said first group, respectively, comprises a fragment antigen-binding (Fab) binding moiety (FBM) coupled to said energy donor, or said energy acceptor including the quencher, said moiety being capable of binding to a Fab region of antibodies in the sample of said animal;
   c) contacting the sample, the first group, and the second group, so as to obtain a reaction mixture, wherein i) the antigen coupled to the energy donor together with the FBM coupled to the energy acceptor including the quencher or ii) the antigen coupled to the energy acceptor including the quencher together with the FBM coupled to the energy donor, are subsequently altogether bound to said soluble antibody upon obtaining said reaction mixture, and wherein the bioassay method is a proximity assay, such that a specific binding of the antigen, the soluble antibody and the FBM is thereby achieved;
   d) allowing the reaction mixture to react;
   e) forming an energy transfer pair between said energy donor and said energy acceptor including said quencher only when i) the antigen coupled to the energy donor together with the FBM coupled to the energy acceptor including the quencher or ii) the antigen coupled to the energy acceptor including the quencher together with the FBM coupled to the energy donor, are subsequently altogether bound to said soluble antibody upon obtaining said reaction mixture, so as to thereby qualitatively and/or quantitatively determine said energy transfer pair;
   f) exciting the energy donor with radiation having an excitation wavelength, thereby forming an excited antigen-antibody-FBM complex; and g) detecting emission radiation from said excited energy donor, whereby the presence of the soluble antibody is subsequently qualitatively and/or quantitatively determined, wherein said energy transfer pair transfers energy between said energy donor and said energy acceptor including said quencher, and wherein the FBM is selected from the group consisting of protein L, recombinant protein L, and constant heavy chain domain (Ch1) binding protein.

2. The bioassay method according to claim 1, wherein the soluble antibody is a human soluble antibody.

3. The bioassay method according to claim 1, wherein the soluble antibody is an animal, excluding human, soluble antibody.

4. The bioassay method according to claim 1, wherein the detection of the emission radiation is detected from:
   i) the acceptor resulting from energy transfer from the donor, whereby an increased emission signal correlates with an increased level of the soluble antibody in the sample, or
   ii) the donor if a quencher is employed, whereby a decreased emission signal of the donor correlates with an increased level of the soluble antibody in the sample.

5. The bioassay method according to claim 1, wherein in step a) the sample and the group comprising the FBM are contacted, and allowed to react; and then the group, first or second group, comprising the antigen is added.

6. The bioassay method according to claim 1, wherein step a) comprises two consecutive phases,
   i) a first phase wherein the sample is contacted with an immobilized capturing immunoglobulin whereby the soluble antibody of the sample is captured by said capturing immunoglobulin, and thereafter
   ii) a second phase wherein said captured soluble antibody of said sample is contacted with the first group and the second group to obtain the reaction mixture.

7. The bioassay method according to claim 1, wherein step a) comprises addition of a kosmotropic, chaotropic, precipitating, and/or outsalting reagent, selected from the group consisting of ammonium sulphate, polyethylene glycol (PEG), organic solvent, salt, urea, guanidine, acid and base.

8. The bioassay method according to claim 7, wherein the detection of emission is carried out at least twice,
   i) once when a denaturing and/or chaotropic agent is included in the reaction mixture, and
   ii) once when said denaturing and/or chaotropic agent is not included in the reaction mixture, whereby the difference in emissions correlates with the avidity of the soluble antibody if present.

9. The bioassay method according to claim 8, wherein the denaturing and/or chaotropic agent is selected from the group consisting of sodium dodecyl sulphate (SDS), urea, thiocyanate, guanidine and diethylamine.

10. The bioassay method according to claim 1, wherein the bodily fluid is selected from the group consisting of blood, plasma, serum, cerebrospinal fluid, saliva, urine, nasopharyngeal secretion, bronchoalveolar secretion, aspirate fluid, lavage fluid, ocular fluid, pleural fluid, exudate, ascites, semen, bile, effusions and any combination thereof preferably plasma, serum, and cerebrospinal fluid.

11. The bioassay method according to claim 1, wherein the soluble antibody is selected from the group consisting of human immunoglobulins A, D, E, G, including subclasses 1, 2, 3 and 4, and M.

12. The bioassay method according to claim 1, wherein the soluble antibody is selected from the group consisting of antibodies against bacteriological, parasitic, fungal and viral antigens, exogenous antigens, autoantigens, allergens, and tumour antigens.

13. The bioassay method according to claim 1, wherein the energy transfer pair is capable of Förster resonance energy transfer (FRET).

14. The bioassay method of claim 13, wherein the bioassay method uses a bioassay, which is a time-resolved FRET (TR-FRET) assay or a two-photon excitation FRET assay.

15. The bioassay method according to claim 1, wherein the bioassay method uses an assay, which is a luminescent oxygen channelling (LOC) assay.

\* \* \* \* \*